(12) United States Patent
Kuchino et al.

(10) Patent No.: US 7,843,678 B2
(45) Date of Patent: Nov. 30, 2010

(54) PHOTOELECTRON GENERATING PLATE, NEGATIVE PARTICLE GENERATING DEVICE AND CHARGE REMOVING DEVICE AND EQUIPMENT USING SUCH DEVICE

(75) Inventors: Kunikazu Kuchino, Nara (JP); Takaiki Nomura, Osaka (JP); Junichi Nawama, Hyogo (JP); Yoshifumi Moriya, Nara (JP)

(73) Assignee: Panasonic Corporation, Osaka (JP)

( * ) Notice: Subject to any disclaimer, the term of this patent is extended or adjusted under 35 U.S.C. 154(b) by 1956 days.

(21) Appl. No.: 10/756,771

(22) Filed: Jan. 14, 2004

(65) Prior Publication Data

US 2004/0144417 A1    Jul. 29, 2004

(30) Foreign Application Priority Data

| | | | |
|---|---|---|---|
| Jan. 16, 2003 | (JP) | | 2003-007993 |
| Jan. 23, 2003 | (JP) | | 2003-014571 |
| Jan. 23, 2003 | (JP) | | 2003-014572 |
| Mar. 24, 2003 | (JP) | | 2003-080264 |
| Apr. 18, 2003 | (JP) | | 2003-113849 |

(51) Int. Cl.
- H01T 23/00    (2006.01)
- H05F 3/00    (2006.01)
- H05F 3/06    (2006.01)

(52) U.S. Cl. ............ 361/213; 361/231; 361/230
(58) Field of Classification Search ............ 361/213, 361/231, 230
See application file for complete search history.

(56) References Cited

U.S. PATENT DOCUMENTS

| | | | | |
|---|---|---|---|---|
| 3,072,978 A | * | 1/1963 | Minto | .......... 96/224 |
| 3,222,562 A | * | 12/1965 | Bennett | .......... 313/231.01 |
| 3,403,252 A | * | 9/1968 | Nagy | .......... 361/231 |
| 4,713,548 A | * | 12/1987 | Kim et al. | .......... 250/423 R |
| 5,133,788 A | * | 7/1992 | Backus | .......... 55/467 |
| 5,418,424 A | * | 5/1995 | Aprile et al. | .......... 315/1 |
| 5,853,866 A | * | 12/1998 | Watanabe et al. | .......... 428/312.8 |
| 6,013,970 A | * | 1/2000 | Nishiwaki et al. | .......... 310/330 |
| 6,103,072 A | * | 8/2000 | Nishiwaki et al. | .......... 204/192.18 |
| 6,106,955 A | * | 8/2000 | Ogawa et al. | .......... 428/469 |
| 6,159,421 A | * | 12/2000 | Fujii | .......... 422/4 |

(Continued)

FOREIGN PATENT DOCUMENTS

| | | |
|---|---|---|
| EP | 0 483 855 | 5/1992 |
| EP | 0 560 379 | 9/1993 |
| EP | 1 035 574 | 9/2000 |
| JP | 63-78471 | 4/1988 |
| JP | 8-10616 | 1/1996 |

(Continued)

OTHER PUBLICATIONS

Korean office action dated Mar. 24, 2010 in corresponding Korean Application No. 10-2004-0003249.

*Primary Examiner*—Stephen W Jackson
*Assistant Examiner*—Zeev Kitov
(74) *Attorney, Agent, or Firm*—Bacon & Thomas, PLLC

(57) ABSTRACT

The photoelectron generating plate includes on a substrate a photoelectron emission layer for emitting photoelectrons by the illumination of the light and having a barrier property. A diffusion of a material of an underlying base member into the photoelectron emission layer is blocked by the barrier layer and thus the surface of the photoelectron emission layer is prevented from being coated by the material of the base member. As a result, temporal reduction in the number of generated negative ions can be considerably ameliorated. In other words, the charge removing device attains a good durability for a long time.

18 Claims, 12 Drawing Sheets

U.S. PATENT DOCUMENTS

| | | | |
|---|---|---|---|
| 6,486,077 B2 * | 11/2002 | Sato | 438/763 |
| 6,774,561 B2 * | 8/2004 | Hirano | 313/503 |
| 6,846,556 B2 * | 1/2005 | Boire et al. | 428/325 |
| 7,049,002 B2 * | 5/2006 | Greenberg et al. | 428/432 |
| 2002/0012615 A1 | 1/2002 | Hwang et al. | |

FOREIGN PATENT DOCUMENTS

| | | | |
|---|---|---|---|
| JP | 8-243434 | 9/1996 | |
| JP | 09-052020 | 2/1997 | |
| JP | 10-057838 | 3/1998 | |
| JP | 10-188780 | 7/1998 | |
| JP | 11-147051 | 6/1999 | |
| JP | 11-165096 | 6/1999 | |
| JP | 2000-153179 | 6/2000 | |
| JP | 2000-167435 | 6/2000 | |
| JP | 2001-187390 | * | 7/2001 |
| JP | 2001-259471 | 9/2001 | |
| JP | 2001-300347 | 10/2001 | |
| JP | 3322267 | 6/2002 | |

\* cited by examiner

ELAPSED TIME (MINUTE)

AIR FLOW

PHOTOELECTRON GENERATING PLATE, NEGATIVE PARTICLE GENERATING DEVICE AND CHARGE REMOVING DEVICE AND EQUIPMENT USING SUCH DEVICE

FIELD OF THE INVENTION

The present invention relates to an apparatus for generating a negative particle; more particularly, to a negative particle generating device using a photoelectron generated by a photoelectric effect.

DESCRIPTION OF THE PRIOR ART

A first conventional negative particle generating device is disclosed in Japanese Examined Patent Application Publication No. H8-10616. In the first conventional negative particle generating device, photoelectrons are generated from a photoelectron emission member by ultraviolet rays from a light source. Entered into the first conventional negative particle generating device is a highly clean air in which minute particles are almost removed by a fan and a dust collecting filter. The generated photoelectrons are captured by the remaining minute particles left in the highly clean air without being removed by the dust collecting filter or the like to thereby create negative particles. And then, the negative particles are emitted in the air.

FIG. 18 represents a second conventional negative particle generating device disclosed in Japanese Patent No. 3322267.

Referring to FIG. 18, photoelectron generating member 51 is installed at an inner portion of vessel 56. Electrical ground 55 is connected to photoelectron generating member 51 and photoelectrons are generated from photoelectron emission member 51 by ultraviolet rays from light source 52. The photoelectrons are captured by molecules of water and oxygen or minute particles such as dust or the like in the air entering through air intake 53 which are running through the surface of photoelectron emission member 51 through flow path control member 57. The captured photoelectrons are emitted to the outside of the second conventional negative particle generating device from air exit 54 as negative particles.

Also, one of conventional negative particle generating schemes uses a discharge type as disclosed in Japanese Patent Laid-Open Publication No. S63-78471. In order to generate negative particles, a discharge in gases is disclosed in the Japanese Laid-Open Publication No. S63-78471.

However, drawback of such conventional negative particle generating devices and scheme is that the number of the photoelectrons generated from photoelectron emission member by ultraviolet rays from light source is reduced with time.

Furthermore, the flow path control member causes a reduction in the flow rate of the air, which in turn reduces the number of the generated photoelectrons to be captured to generate negative particles, resulting in an overall reduction in the amount of the negative particles generated.

Also, ozone generated in the conventional negative particle generating device is hazardous to human body and causes deterioration in members in the conventional negative particle devices.

SUMMARY OF THE INVENTION

It is, therefore, a primary object of the present invention to provide a negative particle generating device for generating negative particles which always maintains a level of the amount of negative particles being generated.

It is another object of the present invention to provide a charge removing device without generating ozone and an equipment using such device.

It is known that a reduction in the number of photoelectrons generated from a photoelectron generating plate is caused by the fact that a surface of a photoelectron emission layer in the photoelectron generating plate is coated by compounds defused through pinholes in the photoelectron emission layer. In order to prevent the reduction in the number of the generated photoelectrons, a photoelectron emission layer of a high barrier property is installed in a photoelectron generating plate to steadily maintain a level of the number of the generated photoelectrons without any reduction therein with time.

In accordance with one aspect of the present invention, there is provided a photoelectron generating plate including on a substrate a photoelectron emission layer for emitting photoelectrons by an illumination of a light thereon and having a barrier property.

In accordance with the photoelectron generating plate of the present invention, a diffusion of a material of an underlying base member into the photoelectron emission layer is blocked and thus a surface of the photoelectron emission layer is prevented from being coated by the material of the base member. As a result, temporal reduction in the number of generated negative ions can be considerably ameliorated. In other words, the photoelectron generating plate attains a good durability for a long time.

Preferably, the substrate is conductive and also can be grounded so that the insufficient number of photoelectrons generated in the photoelectron generating plate by the emission of the photoelectrons can be compensated, and therefore, the photoelectron generating plate attains a good durability and emits many photoelectrons for a long time.

Preferably, the substrate is made of a stainless steel so that a surface diffusion of metal component of the stainless steel by the illumination of the light can be blocked by a surface oxide coating with high density of the stainless steel to thereby ensure the emission of many photoelectrons for a long time.

Preferably, the photoelectron generating plate has a conductive layer between the substrate and the photoelectron emission layer so that, even though the substrate is made of, e.g., an insulation material, the conductive layer is electrically grounded to thereby compensate insufficient photoelectrons generated in the photoelectron generating plate by the emission of the photoelectrons. As a result, the photoelectron generating plate attains a good durability and emits many photoelectrons for a long time.

Preferably, the conductive layer is made of metal of a high conductivity so that the insufficient number of photoelectrons generated in the photoelectron generating plate by the emission of the photoelectrons can be rapidly compensated, and therefore, the photoelectron generating plate attains a good durability and emits many photoelectrons for a long time.

Preferably, a thickness of the photoelectron emission layer is greater than a maximum surface roughness of the underlying layer. Therefore, since photoelectrons can be emitted from whole surface of the photoelectron emission layer and the diffusion of the material of the underlying base member into the photoelectron emission layer can be also blocked, the photoelectron generating plate attains a good durability and emits many photoelectrons for a long time.

Preferably, the photoelectron emission layer is formed by a deposition method to enhance the barrier property so that the photoelectron generating plate attains a good durability and emits many photoelectrons for a long time.

Preferably, the photoelectron emission layer is conductive and is grounded so that the insufficient number of photoelectrons generated in the photoelectron emission layer by the emission of the photoelectrons can be compensated. As a result, the photoelectron generating plate attains a good durability and emits many photoelectrons for a long time.

Preferably, the photoelectron emission layer is made of ceramic material to enhance the barrier property thereof so that the photoelectron generating plate attains a good durability and emits many photoelectrons for a long time.

Preferably, the photoelectron emission layer is made of any one element selected from the group consisting of titanium nitride, titanium carbide, zirconium nitride, zirconium carbide and carbon products whose work function in a photoelectric effect is low so that many photoelectrons can be emitted therefrom and also can be emitted by a visible light. A graphite like carbon has a greater photoelectric effect than a diamond like carbon (DLC) while a layer of the DLC is of such a high density that it has a good durability.

In accordance with another aspect of the present invention, there is provided a negative particle generating device including the photoelectron generating plate mentioned above and a light source for illuminating a light thereon.

In accordance with still another aspect of the present invention, there is provided a negative particle generating device including the photoelectron generating plate mentioned above and a light source for illuminating a light thereon, wherein the substrate in the photoelectron generating plate is electrically grounded.

In accordance with the negative particle generating device of the present invention, the substrate is electrically grounded so that the insufficient number of photoelectrons generated from the photoelectron generating plate by the emission of the photoelectrons can be compensated, and therefore, the negative particle generating device attains a good durability and emits many negative particles for a long time.

In accordance with still another aspect of the present invention, there is provided a negative particle generating device including the photoelectron generating plate above mentioned and a light source for illuminating a light thereto, wherein the conductive layer included in the photoelectron generating plate is electrically grounded.

In accordance with the negative particle generating device of the present invention, the conductive layer is electrically grounded so that the insufficient number of photoelectrons generated from the photoelectron generating plate by the emission of the photoelectrons can be rapidly compensated, and therefore, the negative particle generating device attains a good durability and emits many negative particles for a long time.

Preferably, oxygen is provided onto a surface of the photoelectron generating plate to generate more oxygen contained negative particles.

Also, when the negative particle generating device capable of providing the oxygen contained negative particles is used in an air cleaner, it has a relaxation effect in the air and when used in a refrigerator, it has an anti-oxidizing effect on food and a moisture retaining effect while it has charge removing effect when used in a semiconductor manufacturing equipment.

Also, the elements as mentioned above as well as compounds thereof are effective as the photoelectron emission layer.

Also, a metal including aluminum and the like and an alloy thereof are effective as a conductive substrate. However, the conductivity of the substrate is not essential and so a substrate made of, e.g., glass or plastic or the like, can also be effective.

Furthermore, if the conductive layer is installed between the substrate and the photoelectron emission layer and is electrically grounded, the number of the negative particles emitted can be increased.

Also, a conductive ceramic material like an indium tin oxide (ITO), a tin oxide and the like or compounds thereof are effective as a conductive layer.

In accordance with still another aspect of the present invention, there is provided a photoelectron generating plate including a barrier layer having a barrier property on a substrate and a photoelectron emission layer disposed on the barrier layer and emitting photoelectrons by an illumination of a light thereon.

In accordance with the photoelectron generating plate of the present invention, a diffusion of a material of an underlying base member into the photoelectron emission layer is blocked by the barrier layer and thus the surface of the photoelectron emission layer is prevented from being coated by the material of the base member. As a result, temporal reduction in the number of generated photoelectrons can be considerably ameliorated. In other words, the photoelectron generating plate attains a good durability for a long time.

Preferably, the barrier layer is made of an oxide of Si, Ti, Zr or Al, a nitride of Si or Al, or a composite thereof to significantly enhance the barrier property of the barrier layer so that the photoelectron generating plate attains a durability for a long time.

Preferably, the barrier layer is conductive so that, even though the substrate is made of, e.g., an insulation material, the conductive layer can be electrically grounded to thereby compensate insufficient number of photoelectrons generated from the photoelectron generating plate which emits photoelectrons by the light illumination thereon. As a result, the photoelectron generating plate attains a good durability and emits many photoelectrons for a long time.

Preferably, the barrier layer is made of a nitride or a carbide of Ti or Zr, ITO, or tin oxide, or a composite thereof to significantly enhance the barrier property thereof so that the photoelectron generating plate attains a good durability for a long time.

Preferably, the substrate is conductive and also can be grounded so that the insufficient number of photoelectrons generated from the photoelectron generating plate by light illumination can be compensated by the conductive layer with the barrier property being electrically grounded, and therefore, the photoelectron generating plate attains a good durability and emits many photoelectrons for a long time.

Preferably, the substrate is made of a stainless steel so that a surface diffusion of metal component of the stainless steel by the light illumination can be blocked by a surface oxide coating with high density thereof to thereby emit many photoelectrons for a long time.

In accordance with still another aspect of the present invention, there is provided a negative particle generating device including the photoelectron generating plate mentioned above and a light source for illuminating a light on the photoelectron emission layer in the photoelectron generating plate.

In accordance with still another aspect of the present invention, there is provided a negative particle generating device including: an electrically grounded mesh-shaped photoelectron generating member; and a vessel having therein a light source for illuminating a light to the mesh-shaped photoelectron generating member, wherein the mesh-shaped photoelectron generating member is installed in the vessel such that while the light is illuminated onto the mesh-shaped photoelectron generating member, an air flown through the vessel is directed toward the photoelectron generating member to impinge thereto.

Preferably, the mesh-shaped photoelectron generating member is installed at a location on the air flow path interrupting the air flowing through the vessel such that the air can still flow through the mesh-shaped photoelectron generating member by passing through the mesh holes therein without being blocked and thus a flow path control member is not needed. Therefore, practically, there is no reduction in the amount of the air flow due to the flow path control member and the like. As a result, there is no reduction in the negative particles generated from the negative particle generating device and thus the negative particles can be efficiently generated.

Preferably, the light is an ultraviolet ray whose high energy makes more photoelectrons be easily generated in the photoelectric effect so that more negative particles can be emitted.

Preferably, the mesh-shaped photoelectron generating member using, e.g., noble metal such as gold and the like, is installed on a mesh-shaped conductive member such that it will have a mechanical intensity even though the mesh-shaped photoelectron generating member is a thin layer.

Preferably, the negative particle generating device further includes a ventilator for providing the air to the mesh-shaped photoelectron generating member.

Photoelectron is emitted from the photoelectron generating member by the illumination of the light, leaving a hole in the photoelectron generating member, and the hole is rapidly neutralized by the electrically grounded photoelectron generating member, preventing the photoelectron from returning to the hole. However, even though the photoelectron generating member is electrically neutralized, an electrostatic image force, though weak, works between the photoelectron and the photoelectron generating member so that the electron tends to return to the hole. It is found that a ventilation is effective to rapidly separate the generated photoelectron from the photoelectron generating member. More specifically, a molecule in the air blown from the ventilator to the photoelectron generating member collides with the generated photoelectron to thereby move it further away from the photoelectron generating member, i.e., from the hole, so that it becomes more difficult for the generated photoelectron to return to the hole. As a result, the photoelectron is efficiently generated from the negative particle generating device.

In accordance with still another aspect of the present invention, there is provided a charge removing device including: a light source emitting a light of a wavelength not less than about 200 nm; a photoelectron generating plate for emitting photoelectrons by an irradiation of the light from the light source; and a ventilator for blowing a gas including at least oxygen to make the gas run near a surface of the photoelectron generating plate, wherein the gas running near the surface of the photoelectron generating plate illuminated by the light from the light source is sprayed to a target member to thereby remove a positive charge therefrom.

In accordance with the charge removing device of the present invention, ozone is not produced and negative particles having oxygen can be simply emitted. Also, when the negative particles are sprayed to the target member, the positive charge thereof can be removed.

Preferably, the surface of the photoelectron generating plate, which emits the photoelectrons when the light is illuminated, also serves as a barrier layer. Alternatively, the photoelectron generating plate may include a barrier layer and a photoelectron emission layer placed thereon, the photoelectron emission layer emitting the photoelectrons when the light is illuminated thereon. Therefore, a diffusion of a material of an underlying base member into the photoelectron emission layer is blocked by the barrier layer and thus the surface of the photoelectron emission layer is prevented from being coated by the material of the base member. As a result, temporal reduction in the number of generated negative ions can be considerably ameliorated. In other words, the charge removing device attains a good durability for a long time.

Preferably, the surface of the photoelectron generating plate is electrically grounded so that positive charges of the photoelectron generating plate caused by the emission of the photoelectrons can be rapidly removed. Therefore, more negative particles can be generated so that plus charges and dust of the target member can be rapidly removed.

In accordance with still another aspect of the present invention, there is provided a vacuum cleaner including the charge removing device mentioned above, wherein the gas from the charge removing device is sprayed to a floor to thereby suck a dust attached to the floor while removing positive charges thereon.

In accordance with the vacuum cleaner of the present invention, the negative particles are sprayed toward the floor so that the floor need not be rubbed by using, e.g., a brush. Furthermore, since ozone is not generated so that the floor is prevented from being damaged and the dust attached to the floor can be removed without making users unpleasant.

In accordance with still another aspect of the present invention, there is provided a vacuum cleaner including the charge removing device mentioned above, wherein the gas from the charge removing device is sprayed toward inside of a dust collecting unit to thereby remove positive charges of a dust collected therein and a wall of the dust collecting unit so that the dust therein can readily be eliminated.

In accordance with the vacuum cleaner of the present invention, the negative particles are sprayed toward inside the dust collecting unit so that user need not rub against the dust collecting unit. Furthermore, since ozone is not generated, the wall of the dust collecting unit, e.g., plastic, is prevented from being damaged and the dust attached to the dust collecting unit can be removed without making the user unpleasant.

In accordance with still another aspect of the present invention, there is provided an air blow device including the charge removing device described above, wherein the gas from the charge removing device is sprayed to a target member of the device with a high pressure to thereby blow off a dust attached to the target member while removing positive charges thereon.

In accordance with the air blow device of the present invention, the negative particles are sprayed toward the target member so that the dust attached thereto can be easily removed without strong blow power. Furthermore, since ozone is not generated, the target member is prevented from being damaged and the dust attached to the target member can be removed without making the user unpleasant.

Preferably, the target member is a semiconductor, a liquid crystal glass or a photo disk. Since the dust of a submicron level should be also removed from the target member, the air blow device is appropriate to carry on the removal.

In accordance with still another aspect of the present invention, there is provided an air shower device including the charge removing device described above, wherein the gas from the charge removing device is sprayed to a human body or a target member with a high pressure to thereby blow off dust attached thereto while removing positive charges thereon.

In accordance with the air shower device of the present invention, the negative particles are sprayed toward the human body so that the dust attached thereto can be easily removed without strong blow power. Furthermore, since ozone is not generated, the human body is prevented from being damaged and the dust attached thereto can be removed without making the person unpleasant.

Also, it is preferable that the photoelectron emission layer is made with a conductive layer or a ceramic layer, more particularly, titanium nitride, titanium carbide, zirconium nitride, zirconium carbide and composite thereof.

Furthermore, a metal including a stainless steel, an aluminum and the like and an alloy thereof are effective as the conductive substrate. In doing this, the surface or the substrate of the photoelectron generating plate can be grounded. Also, even though the substrate, e.g., glass or plastic or the like, is not conductive, it still will be effective. Furthermore, the conductive layer is installed between the substrate and the photoelectron emission to be electrically grounded. Also, metal as well as a conductive ceramic material like an indium tin oxide (ITO), a tin oxide or compounds thereof are effective as the conductive layer.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

Hereinafter, preferred embodiments will now be described in conjunction with the accompanying drawings, but the present invention is not limited thereto.

Embodiment 1

Figure 1:
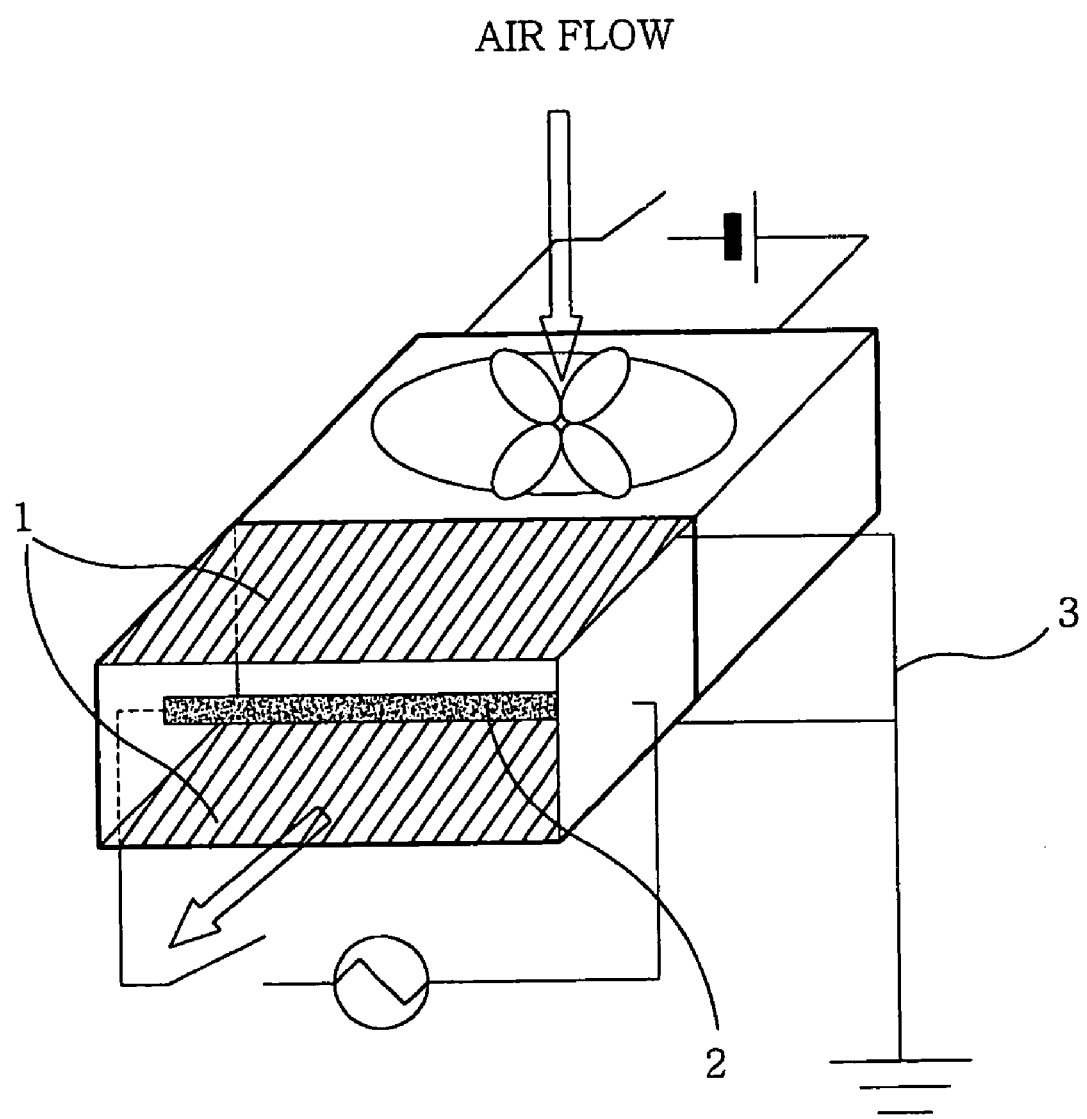
FIG. 1 represents a schematic perspective view of a negative particle generating device in accordance with the present invention.

A negative particle generating device in accordance with a first preferred embodiment of the present invention is described in conjunction with FIG. 1. Reference numeral 1 is a photoelectron generating plate and reference numeral 2 is a lamp (light source) for illuminating a light thereto. Photoelectron generating plates 1 are attached to front portions of an upper and a lower surface of a vent in the negative particle generation device, respectively. A fan is installed at a rear portion of the upper surface of the vent to provide air therefor. Also, without a specific stipulation, electrical ground 3 is connected to a substrate incorporated in photoelectron generating plate 1.

Also, a cold cathode tube with power of 6 W is used as lamp 2 and the air having a flow rate of 200 L/min is provided. Without a specific stipulation, all switches used in the negative particle generating device are turned on.

Figure 8:
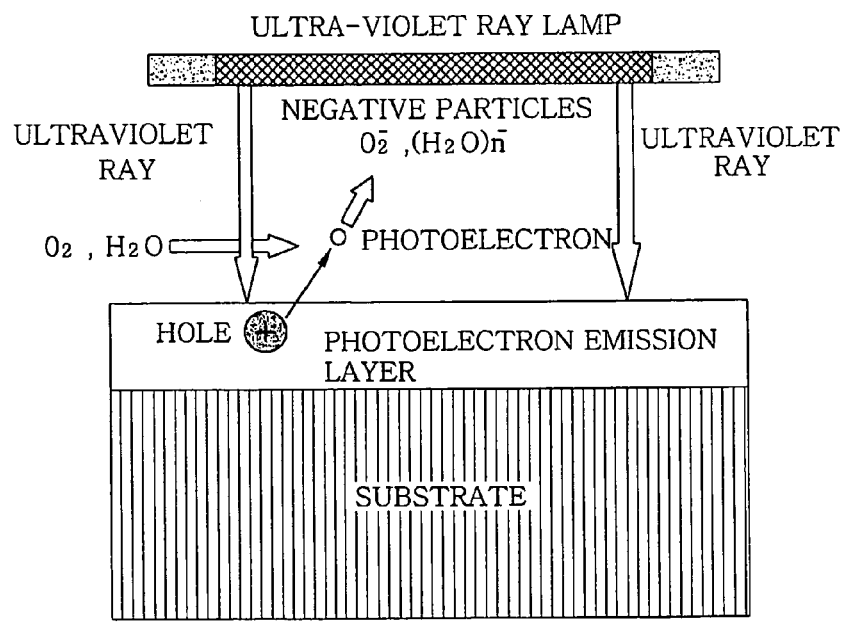
FIG. 8 represents a schematic cross sectional view of a photoelectron generating device incorporating therein an ultraviolet lamp in accordance with the first preferred embodiment of the present invention.

FIG. 8 represents a schematic view of a negative particle generating device incorporating therein an ultraviolet lamp as lamp 2 in accordance with the first preferred embodiment of the invention.

In the first preferred embodiment, photoelectron generating plate 1A was formed by depositing on an acryl substrate a titanium nitride (TiN) layer having a thickness of about 1 μm. Then, photoelectron generating plate 1A was mounted in the negative particle generating device shown in FIG. 1 and the number of negative particles was counted during an operating time. The electrical ground was connected to the TiN layer.

Also, for the comparison with photoelectron generating plate 1A, photoelectron generating plate 1B was formed by depositing on the acryl substrate a gold layer whose thickness was about 1 μm. Then, photoelectron generating plate 1B was mounted in the negative particle generating device shown in FIG. 1 and the number of the negative particles was counted during an operating time. The electrical ground was connected to the gold layer.

Figure 2:
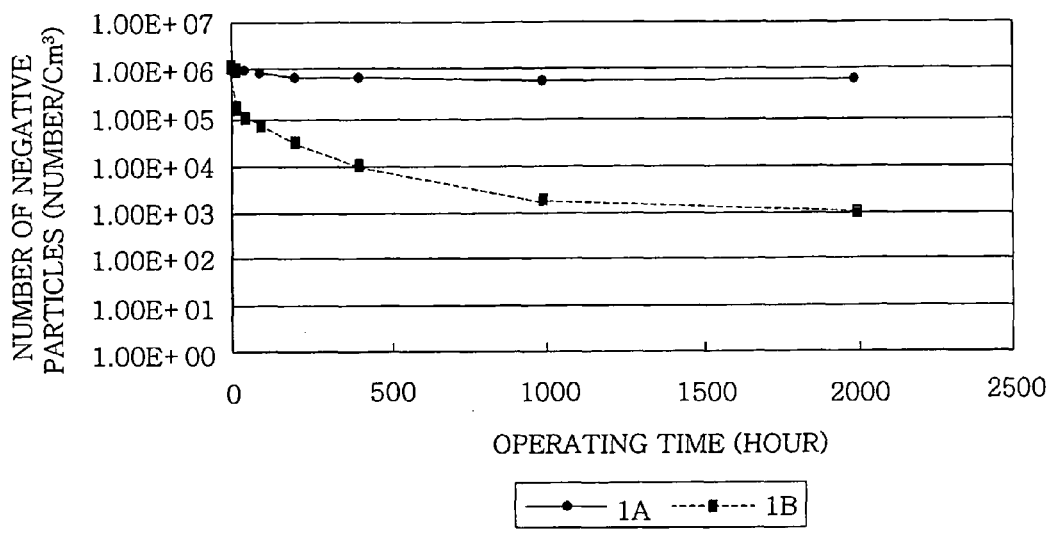
FIG. 2 illustrates a graph of a relationship between an operating time and the number of negative particles generated from a photoelectron generating plate in accordance with a first preferred embodiment of the present invention.

FIG. 2 illustrates a graph of a relationship between the operating time and the numbers of the negative particles respectively generated from photoelectron generating plates 1A and 1B in accordance with the first preferred embodiment of the present invention. Referring to FIG. 2, it is shown that photoelectron generating plate 1A having a barrier property steadily maintains a higher level of the amount of the negative particles in comparison with photoelectron generating plate 1B for a long period.

Embodiment 2

In a second preferred embodiment, photoelectron generating plate 2A was formed by depositing on a brass substrate a titanium nitride (TiN) layer having a thickness of about 1 μm and photoelectron generating plate 2B was formed by depositing on a stainless steel substrate a titanium nitride (TiN) layer whose thickness is about 1 μm. Then, photoelectron generating plates 2A and 2B were mounted in the negative particle generating device shown in FIG. 1, respectively, and respective numbers of negative particles therefrom were counted during the operating time.

Also, for the comparison with photoelectron generating plates 2A and 2B, photoelectron generating plate 2C was formed by depositing on the acryl substrate a TiN layer whose thickness is about 1 μm. Then, photoelectron generating plate 2C was mounted in the negative particle generating device shown in FIG. 1 and the number of the negative particles generated therefrom was counted during an operating time.

Figure 3:
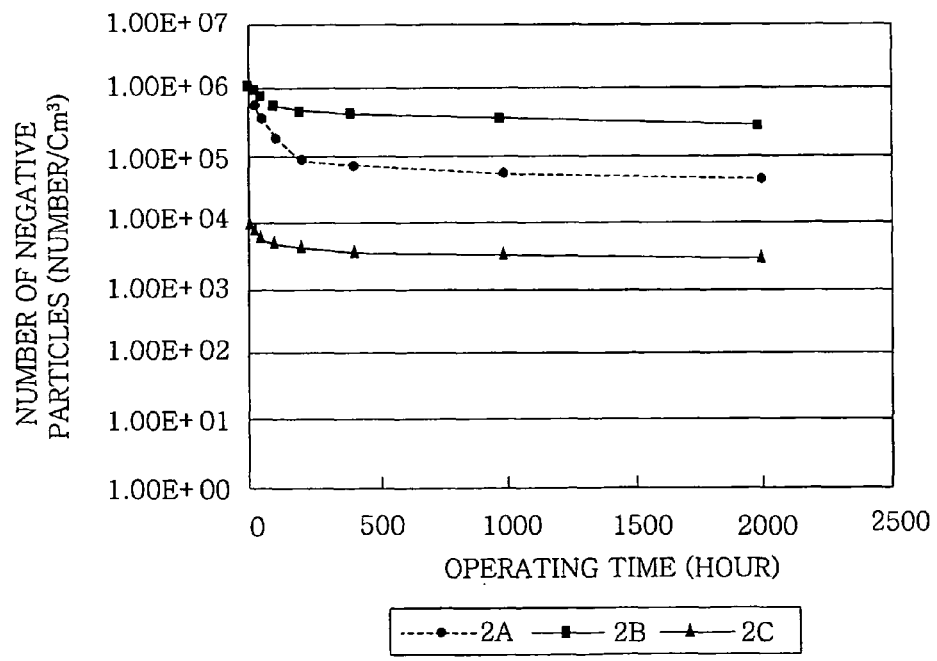
FIG. 3 shows a graph of a relationship between an operating time and the number of negative particles generated from a photoelectron generating plate in accordance with a second preferred embodiment of the present invention.

FIG. 3 shows a graph of a relationship between an operating time and the numbers of negative particles generated respectively from photoelectron generating plates 2A to 2C in accordance with the second preferred embodiment of the present invention. Referring to FIG. 3, it is shown that photoelectron generating plates 2A and 2B, each having a conductive substrate as a base member, emit more negative particles and maintain substantially higher levels of the numbers of the negative particles in comparison with photoelectron generating plate 2C for a long time, thereby demonstrating the effect of the present invention.

Embodiment 3

In a third preferred embodiment, photoelectron generating plate 3A was formed by sequentially depositing on an acryl substrate an aluminum and a titanium nitride (TiN) layer of thickness of about 1 μm. Then, photoelectron generating plate 3A was mounted in the negative particle generating device shown in FIG. 1 and the number of negative particles generated therefrom was counted during an operating time.

Figure 4:
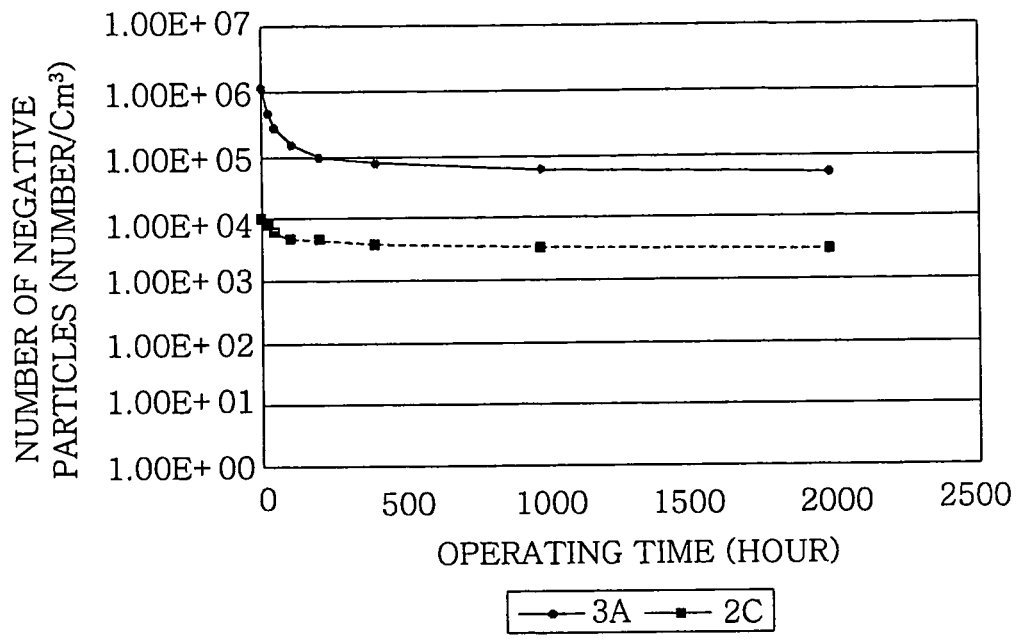
FIG. 4 depicts a graph of a relationship between an operating time and the number of negative particles generated from a photoelectron generating plate in accordance with a third preferred embodiment of the present invention.

FIG. 4 depicts a graph of a relationship between an operating time and the numbers of negative particles generated respectively from photoelectron generating plates 3A and 2C in accordance with the third and the second preferred embodiment of the present invention, respectively. Referring to FIG. 4, it is shown that photoelectron generating plate 3A having a conductive substrate as the base member steadily maintains a larger number of the negative particles in comparison with photoelectron generating plate 2C for a long time, and therefore photoelectron generating plate 3A demonstrates the effect of the present invention.

Embodiment 4

In a fourth preferred embodiment, photoelectron generating plates 4A to 4D were formed by depositing titanium nitride (TiN) layers whose respective thicknesses are about 0.1, 0.5, 1 and 2 μm, on respective stainless steel substrates having maximum surface roughness of about 0.8 μm. Then, photoelectron generating plates 4A to 4D were mounted in the negative particle generating device shown in FIG. 1 and respective numbers of negative particles were counted during an operating time.

Figure 5:
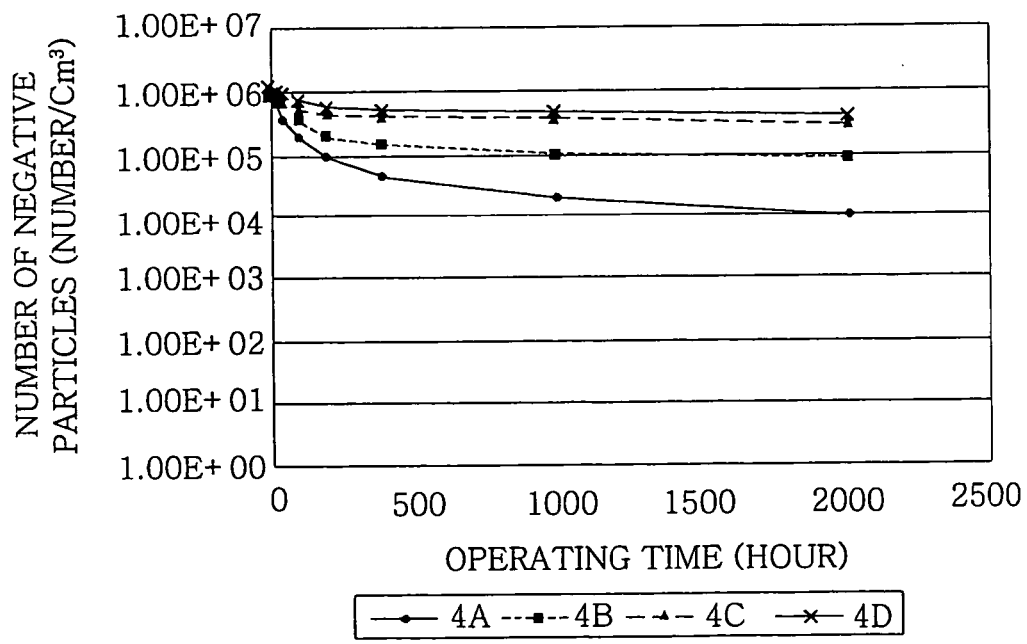
FIG. 5 represents a graph of a relationship between an operating time and the number of negative particles generated from a photoelectron generating plate in accordance with a fourth preferred embodiment of the present invention.

FIG. 5 represents a graph of a relationship between an operating time and the numbers of negative particles generated respectively from photoelectron generating plates 4A to 4D in accordance with the fourth preferred embodiment of the present invention. Referring to FIG. 5, it is shown that photoelectron generating plates 4C and 4D, each having a thickness of the TiN greater than a maximum surface roughness of the stainless steel substrate, steadily maintains, respectively, higher levels of the number of the negative particles in comparison with photoelectron generating plates 4A and 4B for a long time, and therefore photoelectron generating plates 4C and 4D demonstrate the effect of the present invention.

Also, for the comparison with photoelectron generating plate 4C, photoelectron generating plate 4E was formed by sputtering a titanium nitride layer of a thickness of about 1 μm on the stainless steel substrate having a maximum surface roughness of about 0.8 μm. Then, photoelectron generating plate 4E was mounted in the negative particle generating device shown in FIG. 1 and the number of the negative particles was counted during an operating time.

Figure 6:
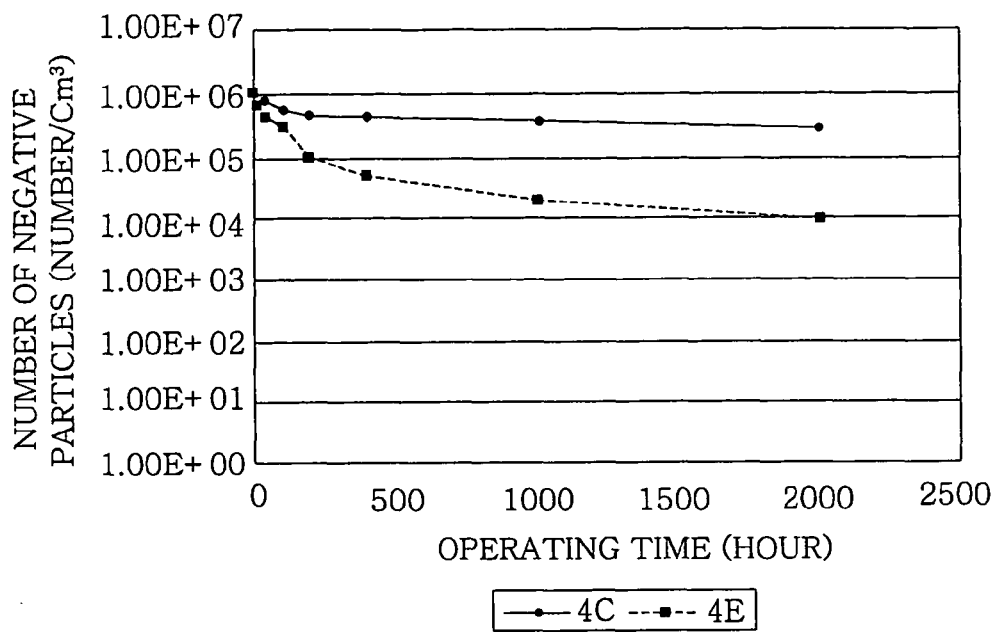
FIG. 6 represents another graph of the relationship between an operating time and the number of negative particles generated from a photoelectron generating plate in accordance with the fourth preferred embodiment of the present invention.

FIG. 6 represents another graph of the relationship between an operating time and the numbers of negative particles generated respectively from photoelectron generating plates 4C and 4E in accordance with the fourth preferred embodiment of the present invention. Referring to FIG. 6, it is shown that photoelectron generating plate 4C steadily maintains a higher level of the number of the negative particles in comparison with photoelectron generating plate 4E for a long time, and therefore demonstrates the effect of the present invention.

Embodiment 5

In a fifth preferred embodiment, photoelectron generating plates 5A and 5B were formed by depositing a graphite and a diamond like carbon (DLC) layer whose respective thicknesses are about 1 μm on the stainless steel substrates having maximum surface roughness of about 0.8 μm, respectively. And, lamp 2 in the negative particle generating device shown in FIG. 1 was substituted with a lamp emitting a light whose wavelength is 182 nm and then photoelectron generating plates 5A and 5B were mounted therein and respective numbers of negative particles generated therefrom were counted during an operating time and compared with that from photoelectron generating plate 4C of the fourth preferred embodiment.

Figure 7:
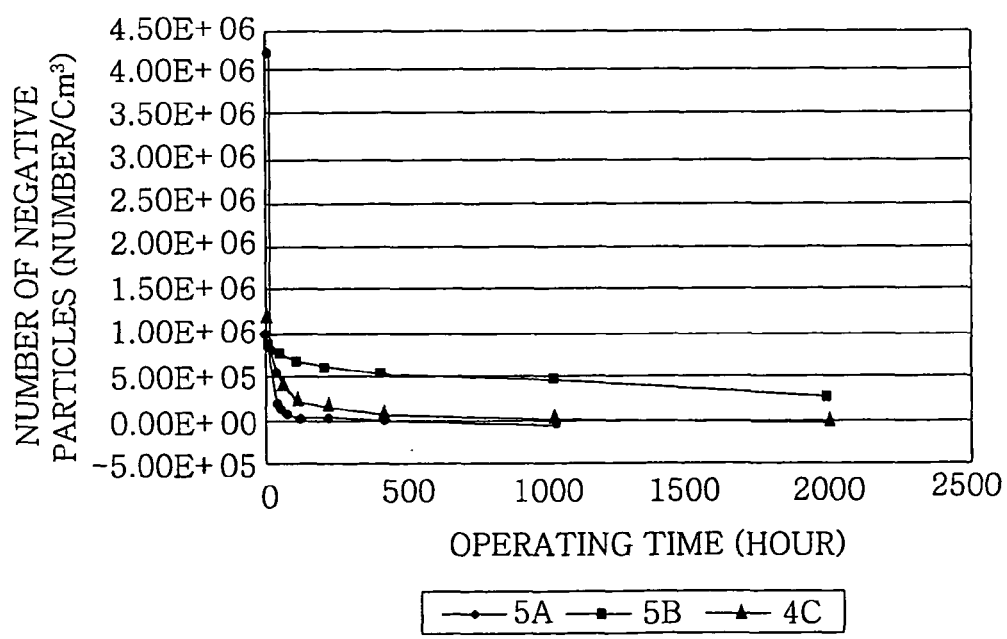
FIG. 7 shows a graph of a relationship between an operating time and the number of negative particles generated from a photoelectron generating plate in accordance with a fifth preferred embodiment of the present invention.

FIG. 7 shows a graph of a relationship between an operating time and the numbers of negative particles generated respectively from photoelectron generating plates 5A, 5B and 4C. Referring to FIG. 7, it is shown that photoelectron generating plate 5A using the graphite emits a huge amount of negative particles in the beginnings of emission thereof while photoelectron generating plate 5B using the DLC generates much less negative particles in the beginnings in comparison with photoelectron generating plate 5A but maintains the level of the amount of the negative particles steadily in comparison with photoelectron generating plates 5A and 4C for a long time.

Embodiment 6

A negative particle generating device in accordance with a sixth preferred embodiment of the present invention is described in conjunction with FIG. 1. Reference numeral 1 is photoelectron generating plate and reference numeral 2 is a lamp (light source) for illuminating a light thereto. Photoelectron generating plates 1 are attached to front portions of an upper and a lower surface of a vent in the negative particle generation device, respectively. A fan is installed at a rear portion of the upper surface of the vent to provide air therefor. Also, without a specific stipulation, electrical ground 3 is connected to a substrate incorporated in photoelectron generating plate 1.

Also, a cold cathode tube with power of 6 W is used as lamp 2 and the air having a flow rate of 200 L/min is provided. Without a specific stipulation, all switches used in the negative particle generation device are turned on.

In the sixth preferred embodiment, photoelectron generating plate 6A was formed by sequentially sputtering on an acryl substrate a silica layer of about 1 μm in thickness and then a gold layer having a thickness of about 1 μm. Then, photoelectron generating plate 6A was mounted in the negative particle generating device shown in FIG. 1 and the number of negative particles was counted during an operating time. The gold layer was electrically grounded.

Also, for the comparison with photoelectron generating plate 6A, photoelectron generating plate 6B was formed by depositing on the acryl substrate a gold layer having a thickness of about 1 μm. Then, photoelectron generating plate 6B was mounted in the negative particle generating device shown in FIG. 1 and the amount of the negative particles was counted during an operating time. Also, the gold layer was grounded.

Figure 9:
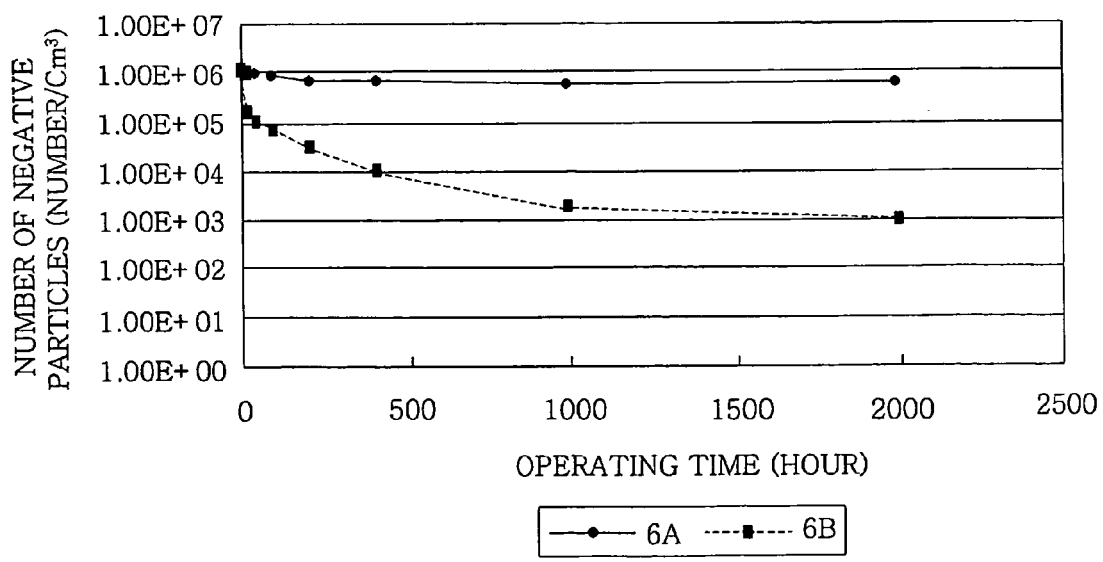
FIG. 9 illustrates a graph of a relationship between an operating time and the number of negative particles generated from a photoelectron generating plate in accordance with a sixth preferred embodiment of the present invention.

FIG. 9 illustrates a graph of a relationship between an operating time and the numbers of negative particles generated respectively from photoelectron generating plates 6A and 6B in accordance with the sixth preferred embodiment of the present invention. Referring to FIG. 9, it is shown that photoelectron generating plate 6A having a barrier property maintains a substantially larger amount of the negative particles in comparison with photoelectron generating plate 6B for a long time.

Embodiment 7

In a seventh preferred embodiment, photoelectron generating plate 7A was formed by sequentially depositing on an acryl substrate a titanium nitride layer of thickness of about 1 μm and a gold layer of thickness of about 1 μm. Then, photoelectron generating plate 7A was mounted in the negative particle generating device shown in FIG. 1 and the amount of negative particles therefrom was counted during an operating time. Also, the titanium nitride layer was grounded.

Also, for the comparison with photoelectron generating plate 7A, photoelectron generating plate 7B was formed by sputtering on the acryl substrate a silica layer of thickness of about 1 μm and then depositing a gold layer having a thickness of about 1 μm thereon. Then, photoelectron generating plate 7B was mounted in the negative particle generating device shown in FIG. 1 and the number of the negative particles generated therefrom was counted during an operating time. Also, the silica layer was grounded.

Figure 10:
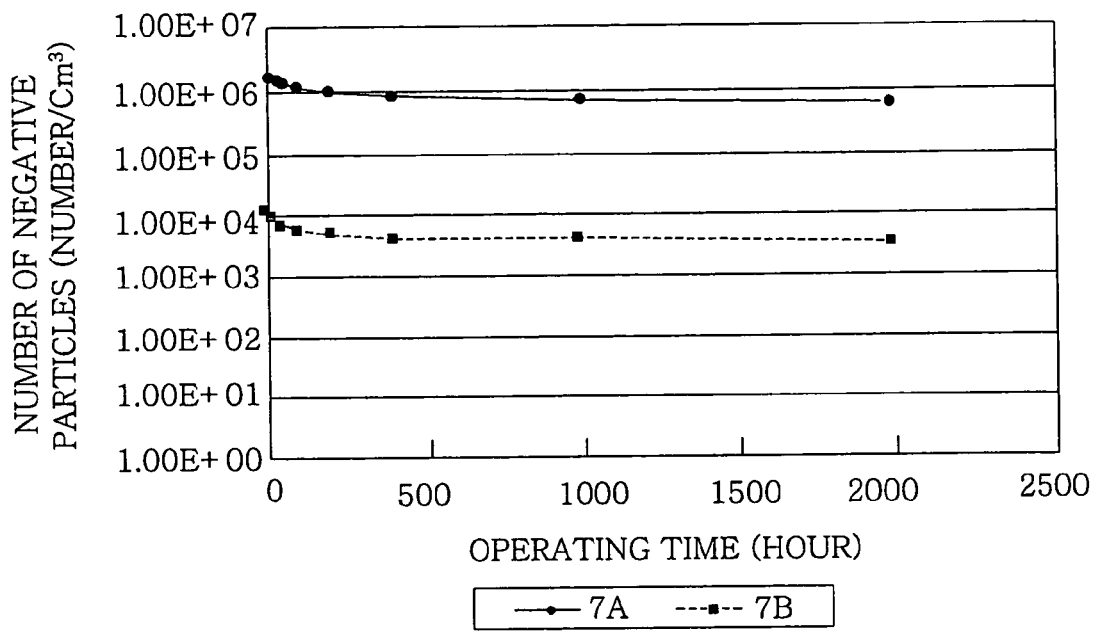
FIG. 10 shows a graph of a relationship between an operating time and the number of negative particles generated from a photoelectron generating plate in accordance with a seventh preferred embodiment of the present invention.

FIG. 10 shows a graph of a relationship between an operating time and the numbers of negative particles generated respectively from photoelectron generating plates 7A and 7B in accordance with the seventh preferred embodiment of the present invention. Referring to FIG. 10, it is shown that photoelectron generating plate 7A having a conductive substrate as a base member maintains a substantially larger amount of the negative particles for a long time in comparison with photoelectron generating plate 7B.

Embodiment 8

In a eighth preferred embodiment, photoelectron generating plate 8A was formed by sequentially depositing on a brass substrate a titanium nitride layer of thickness of about 1 μm and a gold layer having a thickness of about 1 μm and photoelectron generating plate 8B was formed by sequentially depositing on a stainless steel substrate a titanium nitride layer of thickness of about 1 μm and a gold layer having a thickness of about 1 μm. Then, photoelectron generating plates 8A and 8B were mounted in the negative particle generating device shown in FIG. 1 and the respective negative particles generated therefrom were counted during an operating time.

Also, for the comparison with photoelectron generating plate 8A, photoelectron generating plate 8C was formed by sequentially depositing on an acryl substrate a TiN layer of thickness of about 1 μm and a gold layer of thickness of about 1 μm. Then, photoelectron generating plate 8C was mounted in the negative particle generating device shown in FIG. 1 and the number of the negative particles generated therefrom was counted during an operating time.

Figure 11:
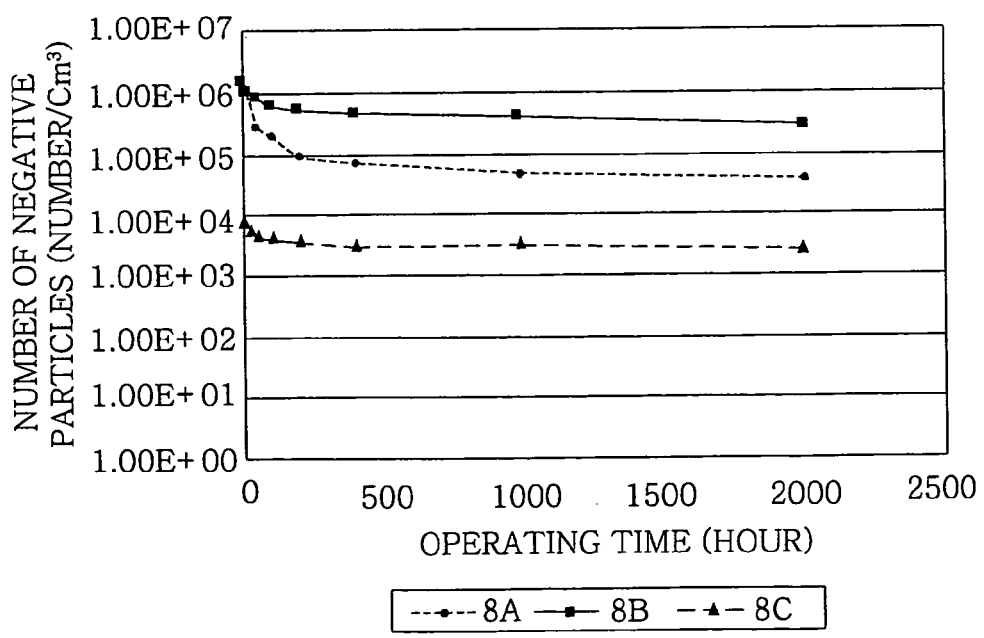
FIG. 11 shows a graph of a relationship between an operating time and the number of negative particles generated from a photoelectron generating plate in accordance with an eighth preferred embodiment of the present invention.

FIG. 11 shows a graph of a relationship between an operating time and the numbers of negative particles generated respectively from photoelectron generating plates 8A to 8C in accordance with the eighth preferred embodiment of the present invention. Referring to FIG. 11, it is shown that photoelectron generating plates 8A and 8B, each having the conductive substrate, maintains substantially larger amount of the negative particles for a long time in comparison with photoelectron generating plate 8C.

Embodiment 9

Figure 12:
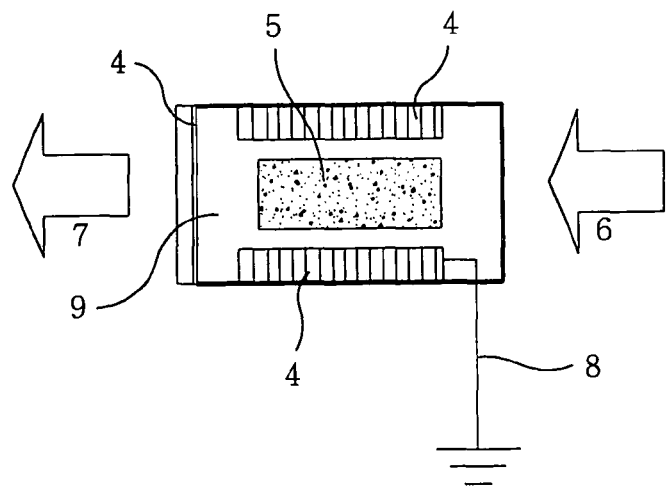
FIG. 12 illustrates a schematic cross sectional view of a negative particle generating device in accordance with a ninth preferred embodiment of the present invention.

FIG. 12 illustrates a schematic cross sectional view of a negative particle generating device in accordance with a ninth preferred embodiment of the present invention. Referring to FIG. 12, mesh-shaped photoelectron generating members 4 are disposed on an inner surface of cylindrical vessel 9 and near to air exit 7. Mesh-shaped photoelectron generating member 4 near to air exit 7 is substantially perpendicular to a direction of the air flow. Electrical ground 8 is connected to mesh-shaped photoelectron emission member 4 on the inner surface of vessel 9. Photoelectrons are generated from mesh-shaped photoelectron generating member 4 by ultraviolet rays or the like from light source 5. The photoelectrons are captured by molecules of water and oxygen or minute particles such as dust or the like in the air entering through air intake 6. The captured photoelectrons are emitted to the outside of the negative particle generation device from air exit 7 as negative particles.

In the ninth preferred embodiment, mesh-shaped photoelectron generating member 4 is made of one or more elements selected from the group consisting of Au, Pt, Ag, Cu, a stainless steel and TiN. Since mesh-shaped photoelectron generating member 4 has a low work function and can efficiently emit the photoelectrons from its surface by light, it is appropriate to use the mesh-shaped photoelectron generating member 4 to efficiently generate the negative particles.

Also, electrical ground 8 is connected to photoelectron generation member 4. Positive holes are created at places from which the photoelectrons are emitted on photoelectron generation member 4 by a photoelectric effect and an electric attractive force works between the positive holes and the photoelectrons. The generated photoelectrons tend to be adsorbed in the positive holes of photoelectron generation member 4 again by the electric attractive force. However, since electrons are supplemented in the positive holes by means of electrical ground of photoelectron generation member 4, the generated photoelectrons are prevented from returning to the positive holes and thus there will be no reduction in the number of negative particles generated.

Hereinafter, an effect of the ninth preferred embodiment of the present invention is described with respect to the following experimental example.

Vessel 9 has a diameter of 3 cm and a length of 7 cm and mesh-shaped photoelectron generating member 4 was made of a gold layer having a thickness of 0.1 mm. Also, an ultraviolet lamp with a power of 3 W was used as light source 5.

Electrical ground 8 was connected to mesh-shaped photoelectron generating member 4 and then experiment was performed in order to evaluate a performance thereof in accordance with the ninth preferred embodiment of the invention. The ultraviolet lamp as light source 5 was turned on. The number of the generated negative particles was counted by using an ionmeter at a location apart from air exit 7 by about 1 cm, at every two minutes during ten minutes and per unit volume.

Figure 18:
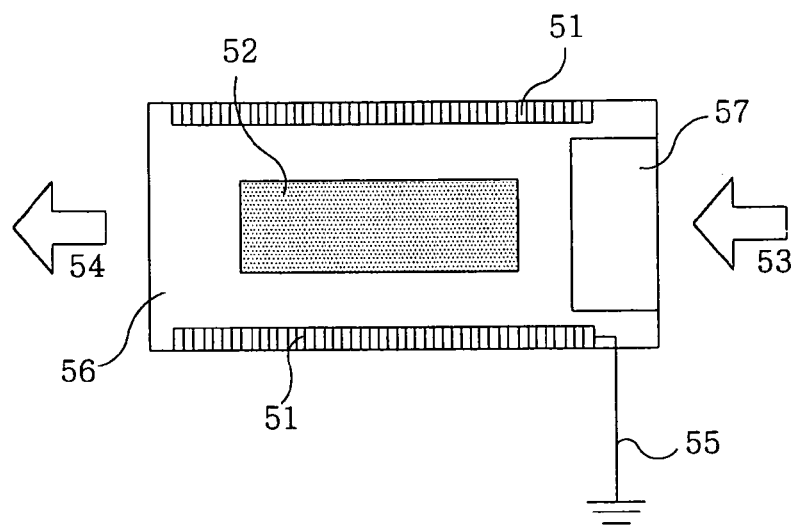
FIG. 18 represents a schematic cross sectional view of a conventional negative particle generating device.

Meanwhile, same experiment was performed to measure the generated negative particles using the conventional negative particle generating device shown in FIG. 18. The results of the above experiments are shown in FIG. 13.

Figure 13:
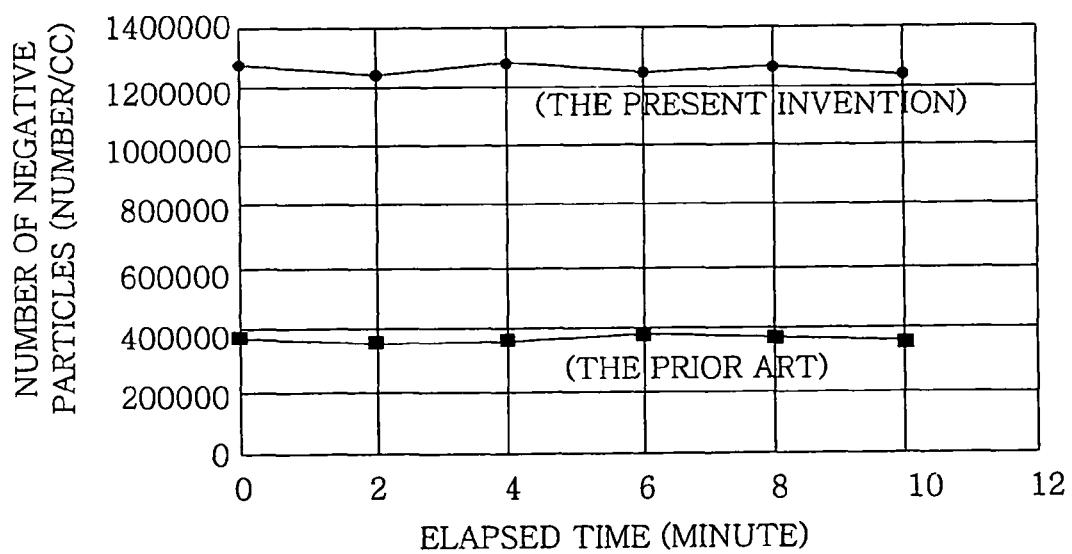
FIG. 13 represents a graph of a relationship between an operating time and the number of negative particles generated from a photoelectron generating plate in accordance with the ninth preferred embodiment of the present invention compared with that in the prior art.

As can be shown from FIG. 13, the negative particle generating device in accordance with the ninth preferred embodiment of the invention steadily emits more negative particles than those of the conventional negative particle generating device shown in FIG. 18.

Embodiment 10

Figure 14:
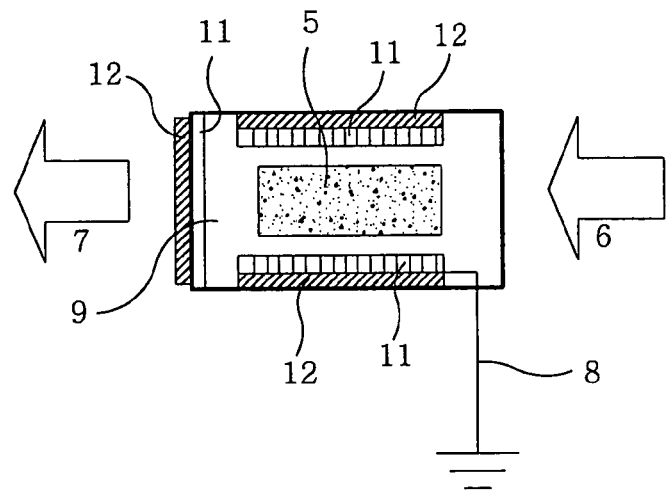
FIG. 14 illustrates a schematic cross sectional view of a negative particle generating device in accordance with a tenth preferred embodiment of the present invention.

FIG. 14 illustrates a schematic cross sectional view of a negative particles emission device in accordance with a tenth preferred embodiment of the invention. Referring to FIG. 14, configurations of the negative particle generating device in this embodiment are identical to those of the ninth embodiment except that mesh-shaped photoelectron generating member 11 is disposed on a surface of mesh-shaped conductive member 12. Therefore, like parts appearing in the ninth preferred embodiment are designated by like reference numerals and detailed explanation thereof will be omitted.

In the tenth preferred embodiment, mesh-shaped photoelectron generating member 11 is made of one or more elements selected from the group consisting of Au, Pt, Ag, Cu, stainless steel and TiN. Since mesh-shaped photoelectron generating member 11 has a low work function and can efficiently emit the photoelectrons from surface thereof by ultraviolet rays, it is useful to efficiently generate the negative particles.

Also, electrical ground 8 is connected to mesh-shaped conductive member 12. Positive holes are created at places on photoelectron generation member 11 where the photoelectrons are emitted by a photoelectric effect and an electric attractive force works between the positive holes and the photoelectrons. The generated photoelectrons tend to be adsorbed in the positive holes of photoelectron generation member 11 again by the electric attractive force. However, since electrons are supplemented in the positive holes by means of electrical ground of photoelectron generation member 4, the generated photoelectrons are prevented from returning to the positive holes and thus there will be no reduction in the number of negative particles generated.

Hereinafter, an effect of the tenth preferred embodiment of the present invention is described with respect to following example.

Vessel 9 had a diameter of 3 cm and a length of 7 cm, mesh-shaped conductive member 12 was made of a stainless steel layer having a thickness of 0.5 mm and a gold layer was coated thereon as mesh-shaped photoelectron generating member 11. Also, an ultraviolet lamp with a power of 3 W was used as light source 5.

Electrical ground 8 was connected to mesh-shaped conductive member 12 and then experiment was performed in order to evaluate a performance thereof in accordance with the tenth preferred embodiment of the invention. The ultraviolet lamp as light source 5 was turned on. The amount of the generated negative particles was measured by using an ionmeter at a location apart from air exit 7 by about 1 cm, at every two minutes during ten minutes and per unit volume. The result of the above experiment is shown in FIG. 15.

Figure 15:
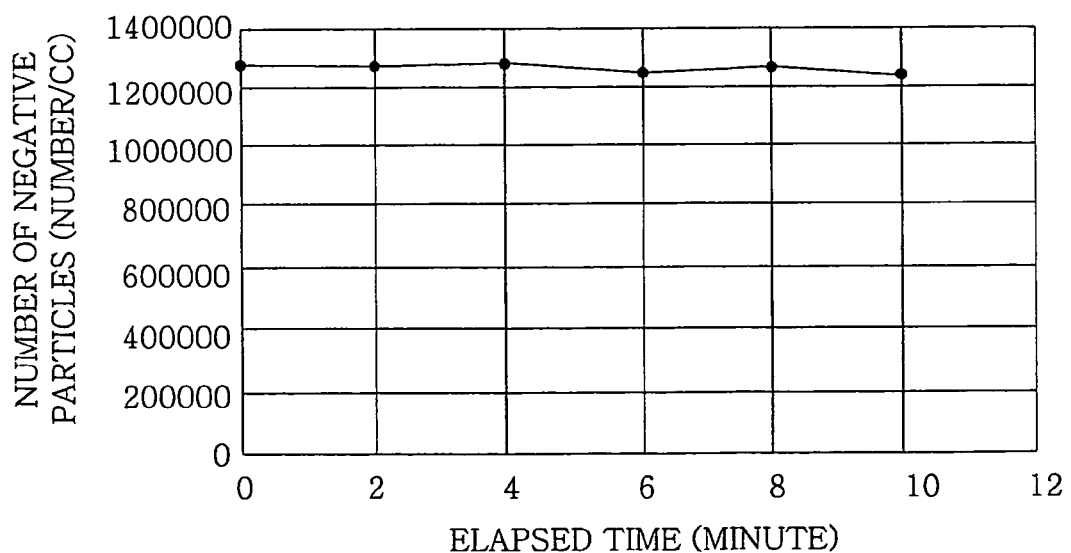
FIG. 15 shows a graph of a relationship between an operating time and the number of negative particles generated from a photoelectron generating plate in accordance with the tenth preferred embodiment of the present invention.

As shown in FIG. 15, it is shown that the negative particle generating device in accordance with the tenth preferred embodiment steadily emits negative particles. As a result, the generation amount of the negative particles is not reduced so that the negative particles can be steadily provided to the air.

Embodiment 11

Figure 16:
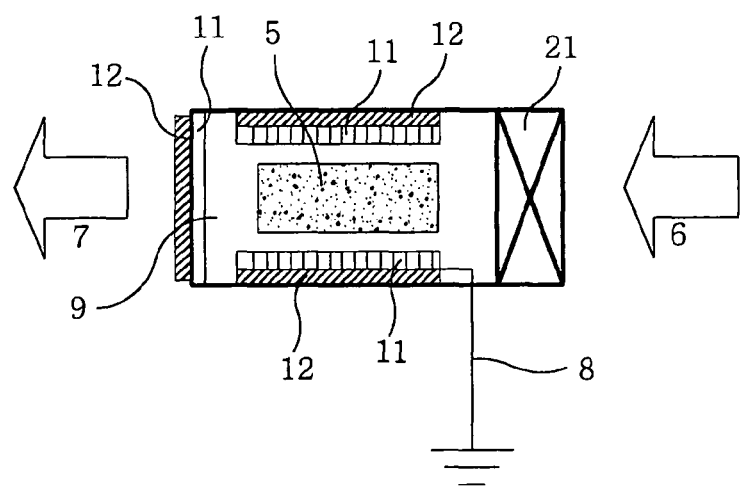
FIG. 16 represents a schematic cross sectional view of a negative particles emission device in accordance with an eleventh preferred embodiment of the present invention.

FIG. 16 illustrates a schematic cross sectional view of a negative particles emission device in accordance with an eleventh preferred embodiment of the invention. Referring to FIG. 16, configurations of the negative particle generating device in this embodiment are identical to those of the tenth embodiment except that ventilator 21 is installed at air intake 6. Therefore, like parts appearing in the tenth preferred embodiment are designated by like reference numerals and detailed explanation thereof will be omitted.

In the eleventh preferred embodiment, mesh-shaped photoelectron generating member 11 is made of one or more elements selected from the group consisting of Au, Pt, Ag, Cu, stainless steel and TiN. Since mesh-shaped photoelectron generating member 11 has a low work function and thus can efficiently emit the photoelectrons from surface thereof by ultraviolet rays, it is useful to efficiently generate the negative particles.

Also, electrical ground 8 is connected to mesh-shaped conductive member 12. Positive holes are created at places on photoelectron generation member 11 where the photoelectrons are emitted by a photoelectric effect and an electric attractive force works between the positive holes and the photoelectrons. The generated photoelectrons tend to be adsorbed in the positive holes of photoelectron generation member 11 again by the electric attractive force. To this problem, since electrons are supplemented in the positive holes by means of electrical ground of photoelectron generation member 4, the generated photoelectrons are prevented from returning to the positive holes and thus there will be no reduction in the negative particles generated.

Hereinafter, an effect of the eleventh preferred embodiment of the present invention is described in conjunction with experimental example 1.

Vessel 9 was of a diameter of 3 cm and a length of 7 cm, mesh-shaped conductive member 12 was made of a stainless steel layer of a thickness of 0.5 mm and a gold layer was coated thereon as mesh-shaped photoelectron generating member 11. Also, an ultraviolet lamp with a power of 3 W was used as light source 5.

Electrical ground 8 was connected to mesh-shaped conductive member 12 and then experiment was performed in order to evaluate a performance thereof in accordance with the eleventh preferred embodiment of the invention. The ultraviolet lamp as light source 5 was turned on and ventilator 21 was operated to thereby emit the negative particles. The amount of the generated negative particles was measured by using an ionmeter at a location apart from air exit 7 by about 1 cm, at every two minutes during ten minutes and per unit volume. The result of the above experiment is shown in FIG. 17.

Figure 17:
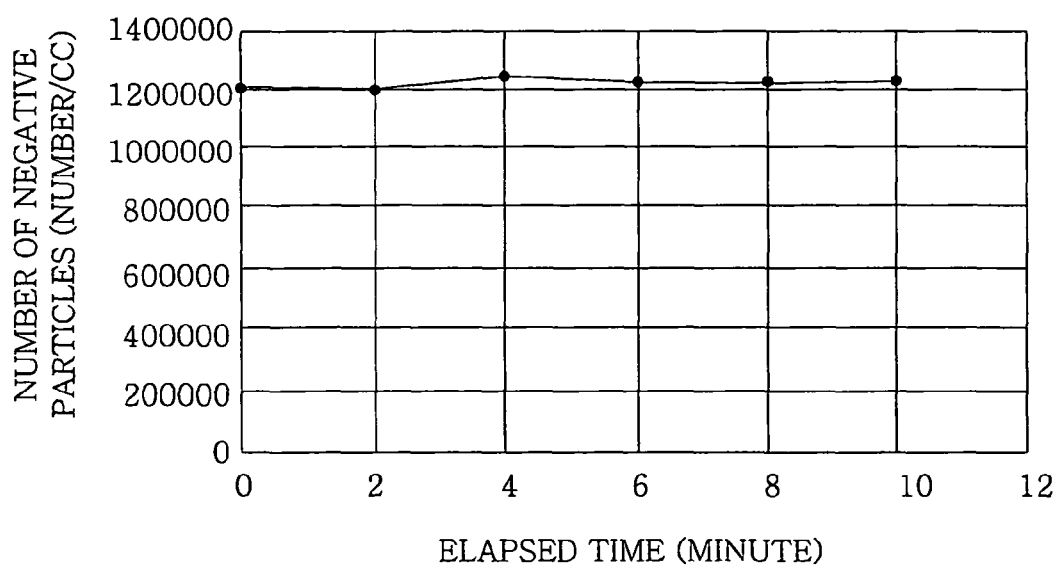
FIG. 17 depicts a graph of a relationship between an operating time and the number of negative particles generated from a photoelectron generating plate in accordance with the eleventh preferred embodiment of the present invention.

As can be seen from FIG. 17, the negative particle generating device in accordance with the eleventh preferred embodiment steadily emitted many negative particles. As a result, by using ventilator 21, the amount of the negative particles generated was increased so that many negative particles could be steadily provided to the air.

Next, the effect of the tenth preferred embodiment of the present invention is described in conjunction with experimental example 2.

In example 2, the amount of generated negative particles was measured in the same manner as described in example 1 except that the mesh-shaped photoelectron emission device incorporating therein mesh-shaped photoelectron generating member 11 made of each of Au, Pt, Ag, Cu, stainless steel and TiN was used. Also, the measurement was performed by the ionmeter at the location apart from air exit 7 by about 1 cm, after two minutes from beginning of operation of the mesh-shaped negative particle generating device and per unit volume. The result of the experiment is shown in Table 1.

TABLE 1

| Species of photoelectron generation material | Number of negative particles (number/cc) |
| --- | --- |
| Au | 270,000 |
| Pt | 120,000 |
| Ag | 90,000 |
| Cu | 50,000 |
| Stainless steel | 10,000 |
| TiN | 420,000 |

As shown in Table 1, it was found that many negative particles were generated in case of using photoelectron generating member made of each of Au, Pt, Ag, Cu, stainless steel and TiN in the negative particle generating device in accordance with this embodiment. Inter alia, when Au, Pt and TiN were used as photoelectron generation material, more negative particles were generated.

Also, the effect of the tenth preferred embodiment of the present invention is described in conjunction with experimental example 3.

In example 3, the number of generated negative particles was measured in the same manner as described in Example 1 except that the mesh-shaped photoelectron emission device incorporating therein mesh-shaped photoelectron generating member 11 made of Au and conductive member made of each of Cu, Al, stainless steel and brass was used. Also, the measurement was performed by the ionmeter at the portion apart from air exit 7 by about 1 cm, after two minutes from the beginning of operation of the mesh-shaped negative particle generating device and per unit volume. The result of the experiment is shown in Table 2.

TABLE 2

| Species of conductive member | Number of negative particles (number/cc) |
| --- | --- |
| Cu | 390,000 |
| Al | 350,000 |
| Stainless steel | 420,000 |
| Brass | 400,000 |

As shown in Table 2, it was found that many negative particles were generated in case of using photoelectron generating member 11 made of Au and conductive member 12 made of Pt, Ag, Cu, stainless steel and TiN in the negative particle generating device in accordance with this embodiment. Inter alia, when stainless steel was used as conductive member 12, more negative particles were generated.

Even though examples 1 to 3 of this embodiment have been described for vessel 9 made of stainless steel of a diameter of 3 cm and a length of 7 cm, it should be apparent to those skilled in the art that vessel 9 is not limited by shape, size, thickness and kinds thereof. For instance, if vessel 9 is of a shape, size, thickness and kinds capable of being incorporated in the negative particle generating device, any vessel 9 can be properly employed.

While examples 2 and 3 of this embodiment have been described for mesh-shaped conductive member made of a stainless steel layer of a thickness of about 0.5 mm, it should be apparent to those skilled in the art that mesh-shaped conductive member is not limited by thickness and kinds thereof. For instance, any mesh-shaped conductive member may be used as long as it is conductive and is capable of carrying the photoelectron generation member.

As described above, the negative particle generation device for emitting the negative particles to the air could be obtained in accordance with the eleventh preferred embodiment. Also, it is needless to say that the negative particle generation device can be applied to an air conditioning equipment, e.g., an air cleaner, an air cooling equipment, a fan heater, a dehumidifier, a humidifier and a deodorizing equipment for removing a skatole and the like.

Also, in this embodiment, while mesh-shaped photoelectron generating member 4 has been disposed both at an inner surface of vessel 9 and near air exit 7, it is not limited thereto as long as it is disposed in the air stream.

Furthermore, even though mesh-shaped photoelectron generating member 4 near air exit 7 is substantially perpendicular to direction of the air stream, it is not limited thereto as long as the air stream in vessel 9 goes through holes therein.

Embodiment 12

A charge removing device in accordance with a twelfth preferred embodiment of the invention is described with reference to FIG. 19. Reference numeral 31 represents a light source having a wavelength not less than about 200 nm and reference numeral 32 is assigned for photoelectron generating plates. Photoelectron generating plates 32 are attached to front portions of an upper and a lower surface of a vent in the negative particle generation device, respectively, and light source is inserted therebetween. Fan 33 is installed at a rear portion of the upper surface of the vent to provide gases including at least oxygen therefor. Also, without a specific stipulation, electrical ground 34 is connected to a substrate incorporated in photoelectron generating plate 32.

Also, a cold cathode tube with power of 6 W is used as lamp 2 and an air of a flow rate of 200 L/min is provided. Without a specific stipulation, all switches used in the charge removing device are turned on.

Example 1

Photoelectron generating plate 9A was formed by coating a gold layer on a brass substrate. Photoelectron generating plate 9A was mounted in the charge removing device shown in FIG. 19 and then the amount of negative particles for neutralizing a positive charged member was measured during an operating time. Electrical ground was connected to the brass substrate.

Example 2

Photoelectron generating plate 9B was formed by depositing a titanium nitride layer on the brass substrate. Photoelectron generating plate 9B was mounted in the charge removing device shown in FIG. 19 and then the amount of negative particles for neutralizing the positive charged member was measured during an operating time. Electrical ground was connected to the brass substrate.

Example 3

Figure 19:
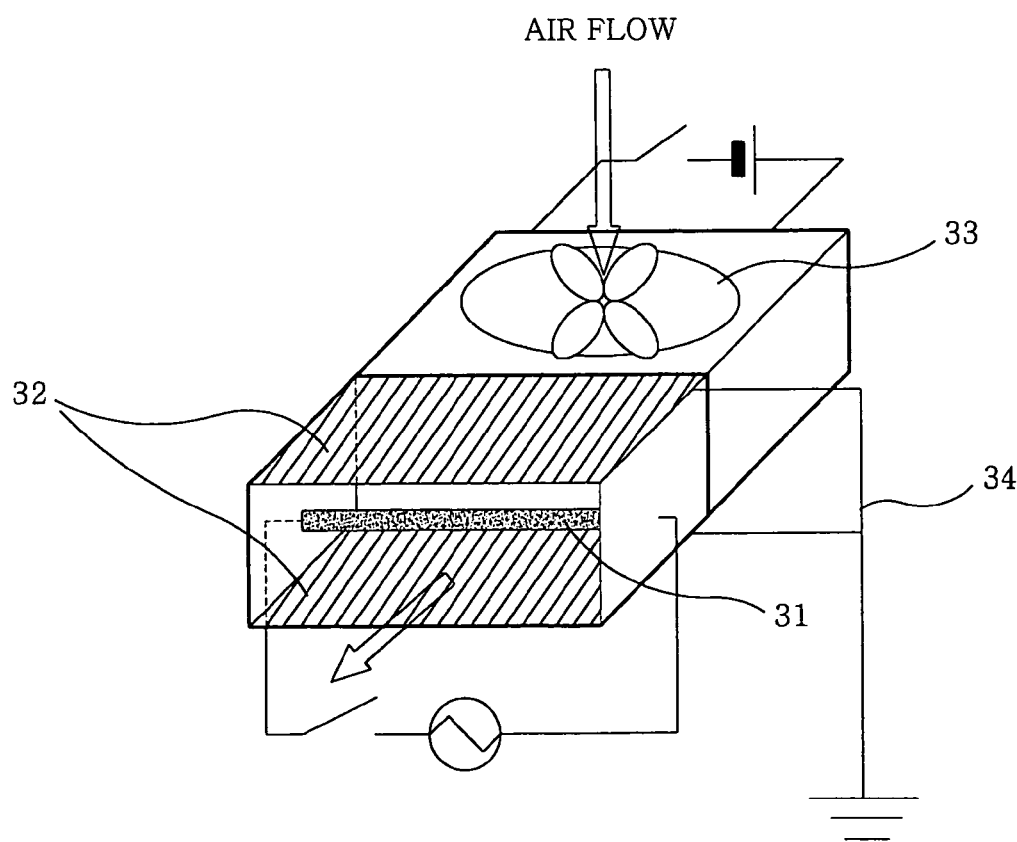
FIG. 19 depicts a schematic perspective view of a charge removing device in accordance with a twelfth preferred embodiment of the present invention.

Photoelectron generating plate 9C was formed by sequentially depositing a SiOx layer and a gold layer on a brass substrate and mounted in the charge removing device shown in FIG. 19. Then, the amount of negative particles for neutralizing a positive charged member was measured during an operating time. Electrical ground was connected to the gold layer.

(Charge Removal of a Positive Charged Resin)

The negative particles generated from charge removing devices including respective photoelectron generating plates 9A to 9C were sprayed to a positive charged member and then an amount of positive charges thereon was measured. As a result, it was found that the amount of the positive charges was reduced, thereby demonstrating the effect of the present invention. Also, a smell of ozone could not be detected.

(Characteristic of Photoelectron Emission Member Having a Barrier Property and Emitting Photoelectrons by a Light Illumination)

Figure 20:
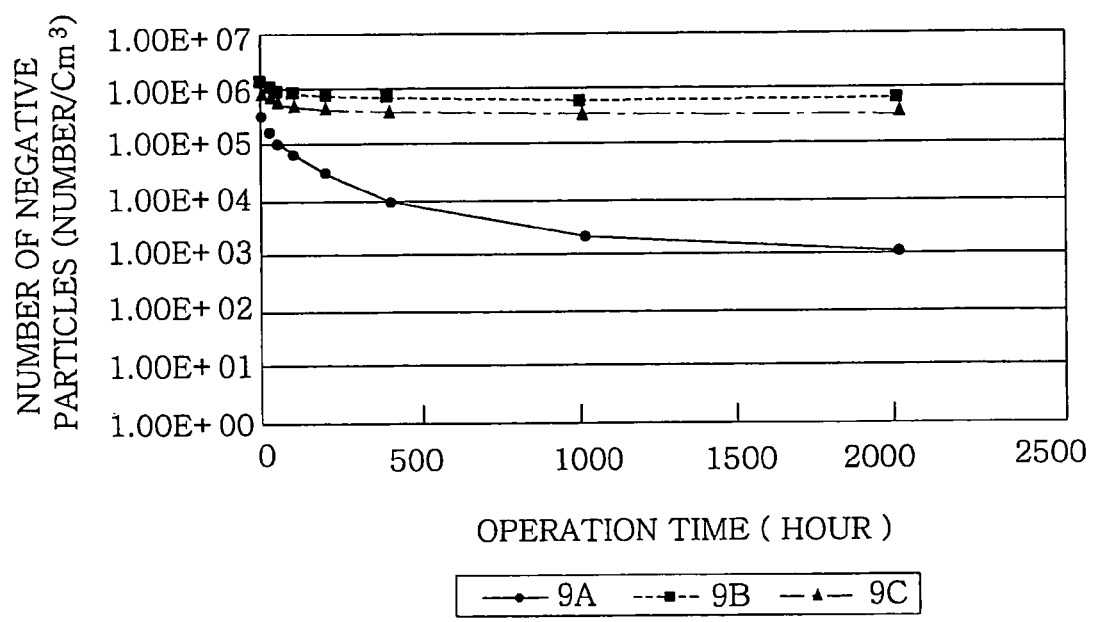
FIG. 20 shows a graph of a relationship between an operating time and the number of negative particles generated from the charge removing device in accordance with the twelfth preferred embodiment of the present invention.

FIG. 20 shows a graph of a relationship between an operating time and the numbers of negative particles generated from the charge removing devices in accordance with the twelfth preferred embodiment of the present invention. Referring to FIG. 20, it is shown that the charge removing devices including therein respective photoelectron generating plates 9B and 9C having a barrier property maintain substantially higher level of the amount of the negative particles for a long time in comparison with the charge removing device including therein photoelectron generating plate 9A. Therefore, the charge removing device including therein respective photoelectron generating plates 9B and 9C demonstrates the effect of the present invention.

Comparative Example 1

Photoelectron generating plate 9D was made by removing electrical ground installed in photoelectron generating plate 9B described in Example 2 and then mounted in the charge removing device shown in FIG. 19. The amount of negative particles for neutralizing the positive charged member as described above was measured during an operating time.

(Amount of Negative Particles for Neutralizing the Positive Charged Member Depending on Electrical Ground)

The amount of negative particles generated for neutralizing the positive charged member was one million number/$cm^3$ from the charge removing device including therein photoelectron generating plate 9B in comparison to 3000 number/$cm^3$ from the charge removing device including therein photoelectron generating plate 9B. Therefore, it is shown that the charge removing device including therein photoelectron generating plate 9B electrically grounded demonstrates the effect of the present invention in contrast to the charge removing device including therein photoelectron generating plate 9D.

Example 4

Figure 21:
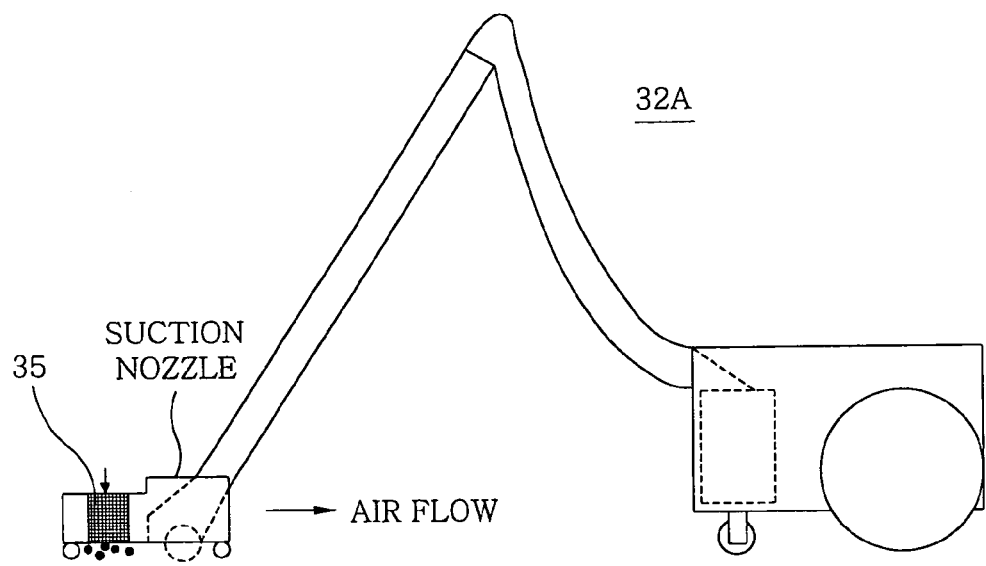
FIG. 21 illustrates a schematic diagram of a vacuum cleaner including a suction nozzle incorporating therein the charge removing device in accordance with Example 4 in the twelfth preferred embodiment of the present invention.

As shown in FIG. 21, vacuum cleaner 32A was fabricated by installing the charge removing device including therein photoelectron generating plate 9B in Example 2 in a bottom side of a suction nozzle, which had a suction efficiency of 200 W. The suction nozzle moved back and forth once on a plastic floor on which a zeolite of 5 g is attached, the plastic floor having the same width as that of the suction nozzle.

Comparative Example 2

Vacuum cleaner 32B was fabricated in the same manner as described in Example 4 except that the charge removing device 35 was not installed therein. The suction nozzle moved back and forth once on a plastic floor on which a zeolite of 5 g is attached, the plastic floor having the same width as that of the suction nozzle.

(Evaluation of a Dust Collecting Capability for the Zeolite)

Collected dust amounts of respective vacuum cleaners 32A and 32B were 4.9 g and 3.9 g. Therefore, it has been proved that vacuum cleaner 32A having charge removing device 35 installed therein in accordance with the present invention has a better dust collecting capability than that of vacuum cleaner 32B. Also, a smell of ozone was not detected by vacuum cleaner 32A.

Example 5

Figure 22:
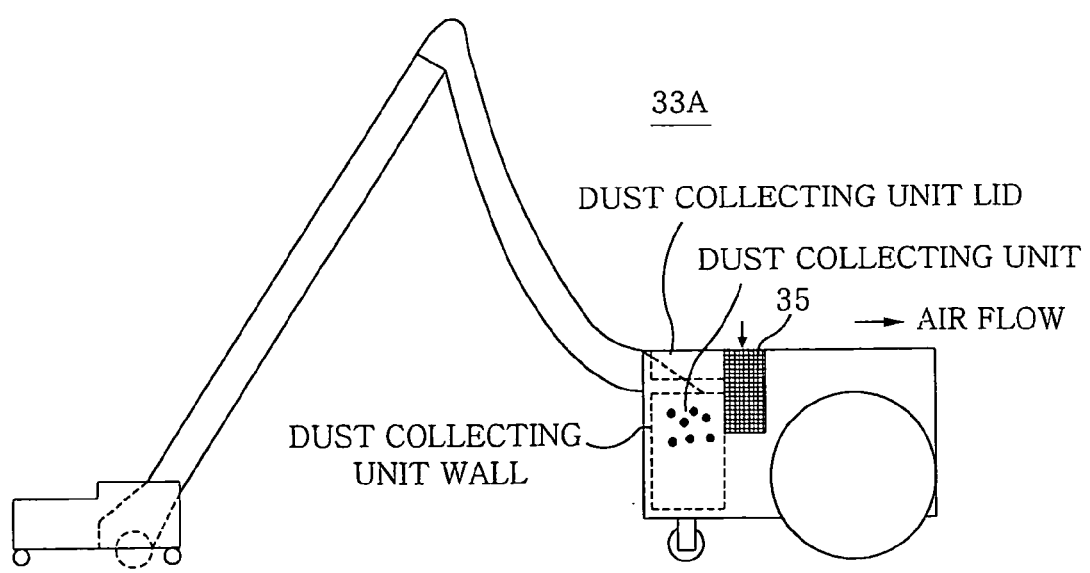
FIG. 22 shows a schematic diagram of a vacuum cleaner including therein a dust collecting unit incorporating therearound the charge removing device in accordance with Example 5 in the twelfth preferred embodiment of the present invention.

As shown in FIG. 22, mounted at a dust collecting unit in a main body of vacuum cleaner 33A having a suction efficiency of 200 W was charge removing device 35 having a same function with the charge removing device having photoelectron generating plate 9B installed therein in Example 2. After a zeolite of 10 g was sucked by vacuum cleaner 33A, a dust collecting unit hood was opened and turned over to thereby measure a free falling amount of the suctioned zeolite.

Comparative Example 3

Vacuum cleaner 33B (not shown) was fabricated in the same manner as described in Example 5 except that the charge removing device 35 was not installed therein. After 10 g of zeolite was sucked by vacuum cleaner 33B, a dust collecting unit hood in vacuum cleaner 33B was opened and turned over to thereby have a free falling amount of the sucked zeolite be measured.

(Evaluation of a Dust Collecting Capability for the Zeolite)

Measured amounts of the zeolite fallen from vacuum cleaners 33A and 33B were about 7.9 g and about 5.9 g, respectively, proving that vacuum cleaner 33A having therein charge removing device 35 installed in accordance with the present invention has a better dust collecting capability than that of vacuum cleaner 33B. Meanwhile, since the sucked zeolite of 10 g can be attached to a suction path, e.g., a hose, the zeolite amounts collected in the dust collecting unit, i.e., 7.9 g and 5.9 g, can be reduced. Therefore, if the gas including negative particles is introduced into, e.g., the hose by means of charge removing device 35, the zeolite amounts collected in the dust collecting unit can be increased. Also, a smell of ozone from vacuum cleaner 33A could not be detected.

Example 6

Air blow device 34A (not shown) was fabricated in such a manner that fan 33 installed in charge removing device 35 including therein photoelectron generating plate 9B was substituted with a compressor for generating a high pressure gas, wherein the compressor had a blow pressure of about 3 kgf/cm$^2$. Glass beads, each being of a diameter of 3 μm and of weight of about 0.1 g, were disposed at a liquid crystal panel glass member of 13.3 inches and then the gas was blown off on the liquid crystal panel glass member by way of air blow device 34A to thereby have a density of remaining glass beads thereon measured.

Comparative Example 4

Air blow device 34B (not shown) was fabricated in the same manner as described in Example 6 except that photoelectron generating plate 9B was not installed therein, wherein air blow device 34B had a suction efficiency of 200 W. By using completely same manner as Example 6, glass beads, each being of a diameter of 3 μm and of weight of about 0.1 g, were disposed at a liquid crystal panel glass member of 13.3 inches and then the gas was blown off on the liquid crystal panel glass member by way of air blow device 34B to thereby have a density of remaining glass beads thereon measured.

(Evaluation of a Removal Capability for Glass Beads)

Measured amount of the glass beads remaining on the liquid crystal panel glass for air blow device 34A was less than 1 number/cm$^2$ and that for air blow device 34B was 4*103 number/cm$^2$, thereby demonstrating that air blow device 34A having therein charge removing device 35 installed in accordance with the present invention has a better removal capability than that of air blow device 34B. Also, the smell of ozone from air blow device 34A could not be detected.

Also, same conclusions were reached for a semiconductor device and a photo disk.

Furthermore, same effect could be also demonstrated for a human body as well as members of the device so that the air blow device 34A in accordance with the present invention is applicable to an air shower used in a semiconductor industry.

As described above, the photoelectron generating plate in accordance with the present invention having a good durability, in other words, without any reduction in the number of negative particles generated therefrom with time for a long time and the negative particle generation device using the same can be realized.

While the invention has been shown and described with respect to the preferred embodiments, it will be understood by those skilled in the art that various changes and modifications may be made without departing from the spirit and scope of the invention as defined in the following claims.

What is claimed is:

1. A photoelectron generating plate comprising on a substrate a photoelectron emission layer for emitting photoelectrons by an illumination of a light and having a barrier property,
    wherein a thickness of the photoelectron emission layer is greater than a maximum surface roughness of an underlying layer thereof, and
    wherein the photoelectron emission layer is made of a ceramic material selected from the group consisting of titanium nitride, titanium carbide, zirconium nitride and zirconium carbide.

2. The photoelectron generating plate of claim 1, wherein the substrate is conductive.

3. The photoelectron generating plate of claim 2, wherein the substrate is made of a stainless steel.

4. A negative particle generating device comprising the photoelectron generating plate of claim 1 and a light source for illuminating a light thereon.

5. The negative particle generating device of claim 4, wherein oxygen gas runs through the surface of photoelectron generating plate to thereby have negative particles generated.

6. A photoelectron generating plate comprising a barrier layer having a barrier property on a substrate and a photoelectron emission layer disposed on the barrier layer and emitting photoelectrons by an illumination of a light thereon,
    wherein a thickness of the photoelectron emission layer is greater than a maximum surface roughness of the barrier layer.

7. The photoelectron generating plate of claim 6, wherein the barrier layer is made of an oxide of Si, Ti, Zr or Al, a nitride of Si or Al, or a composite thereof.

8. The photoelectron generating plate of claim 6, wherein the barrier layer is conductive.

9. The photoelectron generating plate of claim 8, wherein the barrier layer is made of a nitride or a carbide of Ti or Zr, indium tin oxide (ITO), or tin oxide, or a composite thereof.

10. The photoelectron generating plate of claim 8, wherein the substrate is conductive.

11. The photoelectron generating plate of claim 10, wherein the substrate is made of a stainless steel.

12. The photoelectron generating plate of claim 6, wherein the photoelectron emission layer is conductive.

13. A negative particle generating device comprising the photoelectron generating plate of any one of claims 6, 8 and 10 and a light source for illuminating a light on the photoelectron emission layer of the photoelectron generating plate.

14. The negative particle generating device of claim 13, wherein oxygen gas runs through the surface of photoelectron generating plate to thereby have negative particles generated.

15. A negative particle generating device comprising:
a mesh-shaped photoelectron generating member being electrically grounded; and
a vessel including therein a light source for illuminating a light to the mesh-shaped photoelectron generating member;
wherein the light is illuminated to the mesh-shaped photoelectron generating member and simultaneously air runs through a surface of the photoelectron generating member to thereby have negative particles generated,
wherein the mesh-shaped photoelectron generating member is installed in the vessel so that the air flowing in the vessel impinges onto the photoelectron generating member, and
wherein a thickness of the mesh-shaped photoelectron generating member is greater than a maximum surface roughness of an underlying layer thereof.

16. The negative particle generating device of claim 15, wherein the light illuminated to the mesh-shaped photoelectron generating member is ultraviolet ray.

17. The negative particle generating device of claim 15, wherein the mesh-shaped photoelectron generating member is mounted on a mesh-shaped conductive member.

18. The negative particle generating device of claim 15, further comprising a ventilator for providing the air to the mesh-shaped photoelectron generating member.

* * * * *